United States Patent [19]

Faler et al.

[11] 4,365,099

[45] Dec. 21, 1982

[54] PROCESS FOR THE PRODUCTION OF BISPHENOLS

[75] Inventors: Gary R. Faler, Scotia; Ashok K. Mendiratta, Schenectady, both of N.Y.

[73] Assignee: General Electric Company, Schenectady, N.Y.

[21] Appl. No.: 262,739

[22] Filed: May 12, 1981

[51] Int. Cl.³ .................. C07C 39/16; C07C 37/20
[52] U.S. Cl. .................................. 568/726; 568/727; 568/723; 568/775
[58] Field of Search ............... 568/723, 724, 757, 758, 568/759, 727, 749, 775, 726, 764, 763, 728

[56] References Cited

U.S. PATENT DOCUMENTS

| 3,172,916 | 3/1965 | Wagner | 568/728 |
| 3,187,050 | 6/1965 | Duggan et al. | 568/728 |
| 3,351,669 | 11/1967 | Anderson et al. | 568/749 |
| 4,191,843 | 3/1980 | Kwantes et al. | 568/728 |

FOREIGN PATENT DOCUMENTS

| 1017988 | 7/1964 | United Kingdom | 568/726 |
| 1095959 | 9/1966 | United Kingdom | 568/726 |

*Primary Examiner*—Werren B. Lone
*Attorney, Agent, or Firm*—William A. Teoli; James C. Davis, Jr.

[57] ABSTRACT

A method of improving the performance of cationic exchange catalysts used in the production of bisphenols from phenolic compounds and carbonyl compounds by pretreating the phenolic compound with a chelating resin to remove metallic impurities.

14 Claims, No Drawings

PROCESS FOR THE PRODUCTION OF BISPHENOLS

This invention relates to the production of bis(hydroxyaryl) compounds, such as 2,2'-bis(4-hydroxyphenyl) propane, hereinafter referred to as "BPA". More particularly, it relates to an improved continuous process for the production of high purity BPA, which is used as a basic starting material in the preparation of epoxy resins and polycarbonate resins, by a phenol-carbonyl condensation in the presence of a cationic exchange resin.

In the production of the bis(hydroxyaryl) compounds, the phenolic compound is generally present in amounts in excess of two moles per mole of the carbonyl compound. Such bis(hydroxyaryl) or bisphenol compounds referred to above and prepared according to the process of the present invention, may be considered as having the general formula:

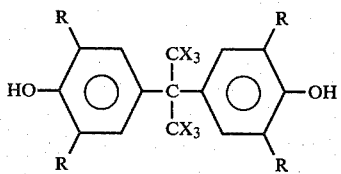 I.

where R is independently selected from the class consisting of hydrogen, monovalent alkyl (including aralkyl) groups of from 1 to 8 carbon atoms (e.g. methyl, ethyl, benzyl, propyl, isopropyl, hexyl, 2-ethylhexyl, etc.); aryl (e.g. phenyl, napthyl, etc.); and alkaryl (e.g. tolyl, etc.); and X is independently selected from the class consisting of hydrogen, fluorine, or alkyl radicals the same as R above. R and X can be the same or different as defined.

The bisphenol corresponding to formula I may be prepared by reacting a phenolic compound having the general formula:

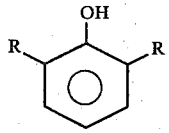 II.

with a carbonyl compound of the formula:

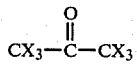 III.

where X and R have the meaning given above and can be the same or different.

By the term "phenolic compounds" as used herein and in the appended claims is meant those organic compounds containing an aromatic radical and one nuclearly bonded hydroxyl group. Phenolic compounds which can be used in the practice of the present invention are, for example, phenol and substituted phenols. Suitable phenolic compounds include phenol, cresols, xylenols, e.g. thymol, carvacrol, cumenol, 2-methyl-6-ethylphenol, 2-ethyl-6-phenylphenol, 2-ethyl-6-methylphenol, 2-methyl-6-tertiary-butylphenol, 2,6-ditertiarybutylphenol, 2,4-diethylphenol, 2,6-dimethylphenol, 2,6-ditertiary-butylphenol, o-phenylphenol, the napthols, phenanthrol, their homologues and analogues, etc. Suitable carbonyl compounds of formula III comprise, for instance, acetone, methylethyl ketone, diethyl ketone, dibutyl ketones, cyclopentanone, acetophenone, benzophenone, hexafluoroacetone, etc.

The specific carbonyl compound employed as a starting material will depend upon the particular bis(hydroxyaryl) compound desired. Particularly suitable compounds in the above-defined class of carbonyl compounds comprise the aliphatic ketones, having from one to twelve carbon atoms in the molecule.

The carbonyl-phenol reaction to produce bisphenols can occur under a variety of acidic conditions. In the production of bis(hydroxyaryl) compounds according to the present invention, a cationic exchange polymeric resin catalyst is generally used to effect the condensation of the particular phenol with the desired carbonyl compound to produce bisphenols.

One of the more attractive catalyst systems used in the production of bis(hydroxyphenyl) compounds employs an insoluble sulfonated polystyrene resin. The primary benefit associated with this catalyst, since it is insoluble in the reaction media, is its ease of removal from the reaction media. However, a disadvantage of this type of catalyst is its low acid concentration relative to the acid concentration of the soluble acid catalysts, which results in a substantially lower catalytic activity. This problem necessitated that the insoluble type ion exchange catalyst be used in conjunction with a rate accelerator such as a mercaptan. The mercaptan group can be attached to the insoluble ion exchange catalyst by means of an ionic bond to the polymer. Mercaptans are well known in the chemical literature to complex with heavy metals. It has been found that the metallic impurities present in commercial phenol sources complex with mercaptan modified insoluble BPA catalysts as described above thus tying up their active sites and decreasing their catalytic effectiveness. A conventional method for metal removal would involve treatment of the ion exchange resin with strong mineral acids; however, this treatment is rigorous enough to also remove the attached mercaptan groups resulting in the destruction of the catalyst system.

It is an object of the present invention to provide a process for the preparation of bis(hydroxyaryl) compounds, such as BPA, by a continuous process which is more economical and produces a bisphenol of formula I which is substantially free of undesirable contaminants which, if present, in polymers tend to give resins, such as polycarbonate resins, of inferior physical properties.

A further object of the present invention is to provide a novel process whereby the cationic exchange resins used as catalysts for making BPA have an extended life as a result of a pretreatment of the phenolic compound prior to reacting the latter with carbonyl compound.

According to the present invention, it has been unexpectedly discovered that passing the phenolic compound through a pretreatment column heated, for instance, to about 30° C. to 80° C., which contains a chelating resin, removes substantially all of the metallic impurities commonly found in commercial phenol sources, resulting in a substantial increase in the life of the cationic polymeric resin. The chelating resin must be insoluble to the phenol compound-carbonyl compound mixture. The chelating resin-containing pretreatment column is placed before the reactor column in the typical BPA process. The pretreatment column can be easily regenerated for example, by employing aqueous mineral acids.

French Pat. No. 2,397,393 discloses that the activity of an acid ion-exchange resin used as a catalyst in the production of bisphenols can be prolonged if a portion of at least one reactor effluent is recycled, preferably back to the first reactor. However, this patent does not recognize that treating the phenolic compound in a separate pretreatment bed with a chelating agent to remove metallic impurities prior to reacting the treated phenolic compound with the carbonyl compound will prolong the life of the cationic ion-exchange resin.

The cation exchange resins utilized in the BPA process utilizing the purified phenol obtained according to the practice of our invention may be any such resin well known in the art and which is substantially insoluble in the reaction mixture at the reaction temperatures employed for making bisphenols, such as BPA, and in any solvent to which the cation exchange resin might be exposed during normal service life. Resin insolubility is generally imparted by cross-linking within the resin structure, but can be influenced and imparted by other factors such as the molecular weight and/or the degree of cryatallinity of the resin or polymer. Suitable resins which can be employed for the condensation in the practice of the present invention include, for example, the sulfonated styrene-divinyl benzene resins, sulfonated cross-linked styrene resins, phenol-formaldehyde sulfonic acid resins, benzene, formaldehyde sulfonic acid resins, sulfonated polystyrene resins, etc. These resins are commercially available under such names as Amberlite 118 by the Rohm and Haas Company, Dowex-50-X-4, by the Dow Chemical Company, Permutit QH by the Permuitt Company, Cempro C-20 by the Chemical Process Company, etc., and are more particularly disclosed in U.S. Pat. No. 3,153,001, issued Oct. 13, 1964, which by reference is made part of the disclosures of the instant invention as to the types of ion exchange resins and methods of preparing the same.

Chelating resins utilized in the present invention may be any chelating resin which is capable of complexing with metallic impurities and which is insoluble in the reactants and solvents being used. The chelating resin can be, for example, polystyrene or divenyl benzene-styrene copolymer resin backbone to which are attached chelating group such as, for example, iminodiacetic acid groups of the formula:

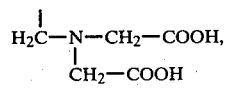
IV.

and mercaptosulfonamide groups of the formula:

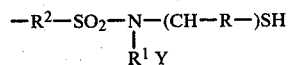
V.

etc. wherein Y is selected from hydrogen, carboxy, and nitrile, R is a divalent $C_{(2-13)}$ organic radical, $R^1$ is a hydrogen or a $C_{(1-14)}$ monovalent alkyl radical and $R^2$ is a trivalent $C_{(6-13)}$ aromatic organic radical. Preferred chelating resins would be polystyrene with iminodiacetic acid groups attached thereto and would contain between 0.2 and 5.0 milliequivalents of iminodiacetic acid and preferably ~1 milliequivalent of iminodiacetic acid per gram of dry catalyst. This preferred resin is commercially available under names such as Dowex A-1 by the Dow Chemical Company, IRC-718 by the Rohm and Haas Company, Chelex-100 by the Bio Rad Company, etc.

In order that those skilled in the art will be better able to understand and practice the invention, the following examples are given by way of illustration and not by way of limitation.

EXAMPLE I

To a 1'×11" glass column was added Amberlite-118 which had been neutralized with 10% 2-mercaptoethyl amine hydrochloride. Through this column at 70° C. was passed an 8:1 molar ratio of phenol and acetone at a weight hourly space velocity (hereinafter referred to as "WHSV") of 4.73 hr$^{-1}$, (wt of feed/hr)/(wt of catalyst). The experiment was allowed to proceed for eight days. Samples of the products were taken daily and analyzed and mole percents conversion to BPA were obtained and are shown below in Table I, Test 1.

In a second test 1'×11" glass column was filled with Chelex-100, polystyrene resin with attached iminodiacetic acid groups. This was heated to 50° C. and phenol was passed through this resin at a WHSV of 60 hr$^{-1}$. To the resultant phenol, acetone was added at a mole ratio of 8:1 phenol:acetone and this mixture was subjected to the same reaction conditions as described above. The reaction was allowed to proceed continuously for eight days. Samples of the products were taken daily for analysis and mole percents conversion to BPA were again obtained and are shown in Table I, Test 2.

TABLE I

MOLE PERCENT CONVERSION OF TREATED AND UNTREATED PHENOL

| TEST 1- UNTREATED PHENOL | | TEST 2- TREATED PHENOL | |
|---|---|---|---|
| TIME (DAYS) | % CONVERSION TO BPA | TIME (DAYS) | % CONVERSION TO BPA |
| 1 | 59.3 | 1 | 58.6 |
| 2 | 58.4 | 2 | 58.5 |
| 3 | 56.3 | 3 | 59.3 |
| 4 | 53.8 | 4 | 59.5 |
| 5 | 53.9 | 5 | 60.0 |
| 6 | 52.4 | 6 | 60.0 |
| 7 | 49.0 | 7 | 58.7 |
| 8 | 47.7 | 8 | 59.0 |

It can be seen from the table that pretreatment of the phenol with a chelating resin to remove metallic impurities substantially increases the useful life of the ion exchange resin used to effect the phenol-carbonyl condensation in the production of bisphenols. The catalyst subjected to the treated phenol showed no deactivation after 8 days while untreated phenol resulted in a decrease of ~20% in catalyst activity to BPA conversion after 8 days.

Other modifications and variations of the present invention are possible in the light of the above teachings. It is, therefore understood that changes may be made in the particular embodiments described above and other chelating agents can be used to pretreat the phenol, all of which are within the full intended scope of the invention as defined in the appended claims.

What we claim as new and desire to secure by Letters Patent:

1. In a method for the condensation of a carbonyl compound selected from the class consisting of, cycloheptanone, acetophenone, benzophenone and compounds of the general formula:

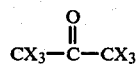

wherein X is independently selected from the class consisting of hydrogen, fluorine, monovalent alkyl groups, from 1 to 8 carbon atoms, aryl groups and alkaryl groups with a phenolic compound of the general formula:

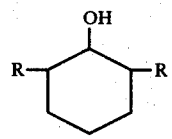

wherein R is independently selected from the class consisting of hydrogen fluorine monovalent alkyl groups from 1 to 8 carbon atoms, aryl groups and alkaryl groups for the production of bis(hydroxyaryl) compounds, whereby at least two moles of said phenolic compound are caused to react with one mole of said carbonyl compound in the presence of a cationic exchange resin in a reaction zone; the improvement comprising pretreating said phenolic compound by contacting said phenolic compound with a chelating resin to remove impurities and thereafter mixing said phenolic compound with said carbonyl compound.

2. A method for the preparation of bis(hydroxyaryl) compounds as in claim 1 wherein the chelating resin has iminodiacetic acid groups attached thereto.

3. The method for the preparation of bis(hydroxyaryl) compounds as in claim 1 wherein the chelating resin has sulfonamide groups attached thereto.

4. The method for the preparation of bis(hydroxyaryl) compounds as in claim 1 wherein the cationic exchange resin is a sulfonated polystyrene resin.

5. The method for making bis(hydroxyaryl) compounds which comprises
(1) pretreating a phenolic compound by passing the phenolic compound through a bed containing a chelating resin;
(2) adding a carbonyl compound to the pre-treated phenolic compound; and
(3) passing the phenolic-carbonyl mixture through a reaction zone containing a neutralized cationic exchange resin to effect a condensation reaction; and
(4) removing the phenolic-carbonyl condensation products.

6. A method for the preparation of bis(hydroxyaryl) compounds as in claim 1 wherein the phenolic compound is phenol and the carbonyl compound is acetone.

7. The method for the preparation of bis(hydroxyaryl) compounds as in claim 5 wherein the phenolic compound is phenol and the carbonyl is acetone.

8. The method of claim 1 wherein the chelating resin is polystyrene or divenylbenzene-styrene copolymer with attached chelating groups.

9. The method of claim 8 wherein the chelating groups are iminodiacetic acid groups.

10. The method of claim 8 wherein the chelating groups are mercapto sulfonamide groups.

11. The method of claim 9 wherein the chelating resin contains between 0.2 and 5.0 milliequivalent of iminodiacetic acid groups per gram of dry catalyst.

12. The method of claim 8 wherein the chelating resin contains ~1 milliequivalent of imiodiacetic acid groups per gram of dry catalyst.

13. A phenolic compound useful in the preparation of bisphenolic compounds which has been treated with a chelating agent to remove impurities in accordance with the method of claim 1.

14. Phenol, useful in the preparation of BPA by the condensation of said phenol and acetone, said phenol having been pretreated with a chelating agent in accordance with the method of claim 1 to remove impurities, whereby in the condensation of said pretreated phenol with acetone the useful life of the condensation catalyst is increased by virtue of said pretreatment.

* * * * *